United States Patent
Dietz et al.

(10) Patent No.: US 6,640,202 B1
(45) Date of Patent: Oct. 28, 2003

(54) ELASTIC SENSOR MESH SYSTEM FOR 3-DIMENSIONAL MEASUREMENT, MAPPING AND KINEMATICS APPLICATIONS

(75) Inventors: Timothy Alan Dietz, Austin, TX (US); Nadeem Malik, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/578,741

(22) Filed: May 25, 2000

(51) Int. Cl.[7] .............................................. G06F 15/00

(52) U.S. Cl. ..................... 702/167; 702/156; 702/161; 342/118; 342/126; 342/146

(58) Field of Search .............................. 702/156, 161, 702/167; 342/118, 126, 146

(56) References Cited

U.S. PATENT DOCUMENTS

| | | | | |
|---|---|---|---|---|
| 5,744,953 A | * | 4/1998 | Hansen | 324/207.17 |
| 5,896,191 A | * | 4/1999 | Beier et al. | 356/35.5 |
| 6,035,398 A | * | 3/2000 | Bjorn | 713/186 |
| 6,487,516 B1 | * | 11/2002 | Amorai-Moriya | 702/152 |

* cited by examiner

*Primary Examiner*—John Barlow
*Assistant Examiner*—Stephen J. Cherry
(74) *Attorney, Agent, or Firm*—Duke W. Yee; Mark E. McBurney; Stephen J. Walder, Jr.

(57) ABSTRACT

An apparatus, method, and system for determining the shape of a three dimensional object. In a preferred embodiment, the apparatus includes an array of sensors and elastic connections between the sensors within the array. When placed over a three dimensional object, the array of sensors deforms to conform to the surface topology of the three dimensional object. The sensors are connected to a data processor in which the data from the sensors is taken to construct a three-dimensional representation of the actual physical three dimensional object.

28 Claims, 5 Drawing Sheets

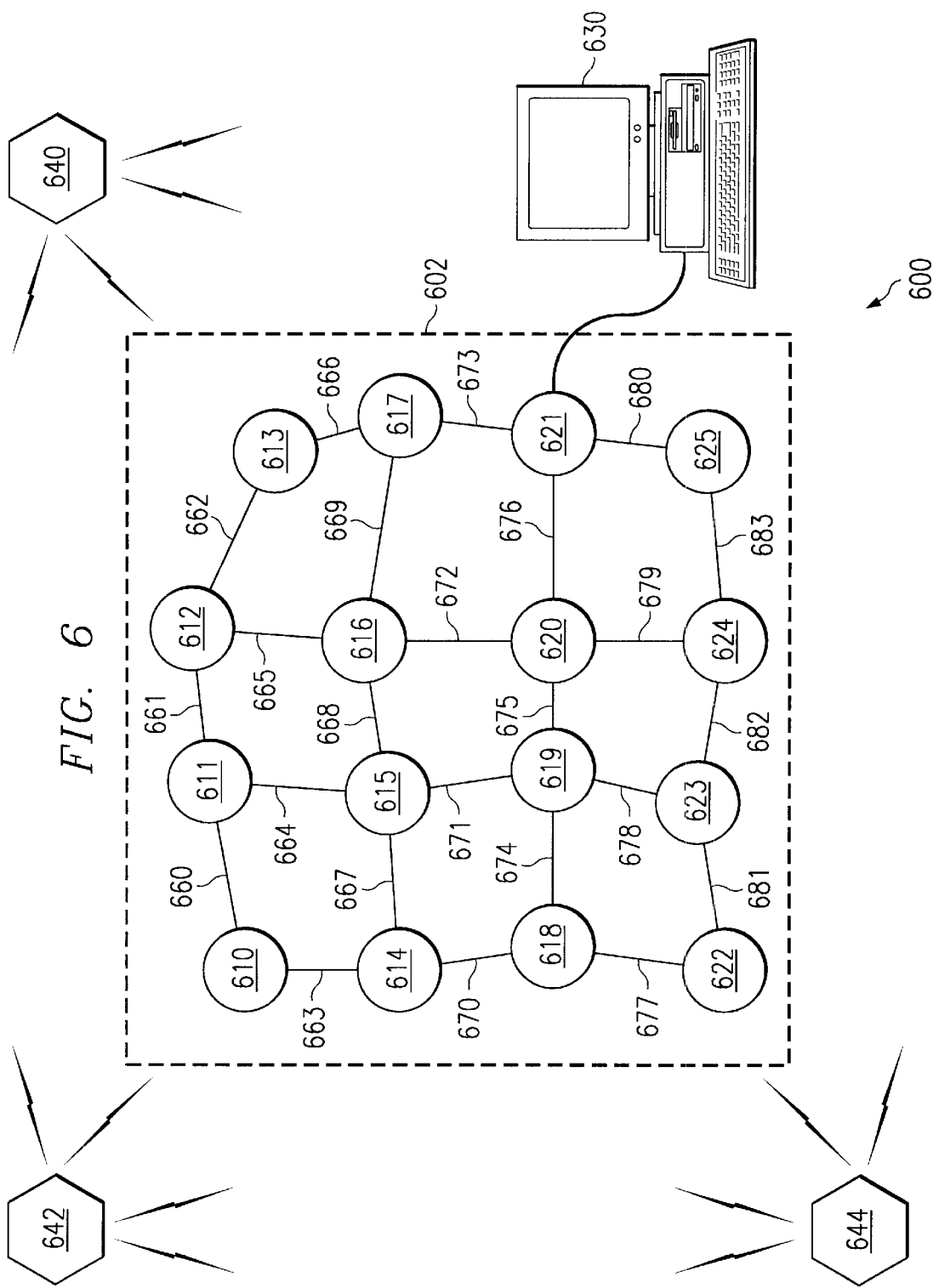

ELASTIC SENSOR MESH SYSTEM FOR 3-DIMENSIONAL MEASUREMENT, MAPPING AND KINEMATICS APPLICATIONS

BACKGROUND OF THE INVENTION

1. Technical Field

The present application relates to a method, system, and apparatus for making 3-dimensional measurements of animate and inanimate objects.

2. Description of Related Art

The unique shapes and proportions of many animate and inanimate objects, especially animate ones with considerable variability in three dimensional space (e.g., the human form), make them difficult to accurately record for a variety of applications. For example, covering objects (e.g., clothing the human form), mapping movements of these objects (e.g., tracing a human form's movements in three dimensional space, say while performing a sporting activity like a golf swing), and analyzing other dimensional characteristics become quite difficult.

In the area of garment manufacturing, a system exists to acquire precise measurements of the human form for use in creating customized clothing. This system requires a very expensive room be built. The room includes multiple light beam sources. A person for whom measurements are needed enters the room and is then scanned by the multiple light beams. The data gathered through this process is used to create measurements which are used in the creation of customized clothing. However, the equipment necessary to perform this procedure is quite large and very expensive, often costing in excess of $300,000 per system.

Another existing technology utilizes electro-optical sensors in conjunction with a glove that a person wears. These devices are capable of measuring flex and movement to some degree and translating it into computer usable data. However, these devices are bulky and require different sizes for different individuals.

Therefore, a method, system, and apparatus that provides a simple and cost effective way to accurately record a wide range of sizes and shapes of such animate and inanimate objects is desirable. Such a solution would open up opportunities for customized clothing, more effective kinematics training methods and a host of other applications that today are costly and only available where there are expensive facilities or limited resources.

SUMMARY OF THE INVENTION

The present invention provides an apparatus, method, and system for determining the shape of a three dimensional object. In a preferred embodiment, the apparatus includes an array of sensors and elastic connections between the sensors within the array. When placed over a three dimensional object, the array of sensors conforms to the surface topology of the three dimensional object. The sensors are connected to a data processor in which the data received from the sensors is used to construct a three-dimensional representation of the actual physical three dimensional object.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

FIG. 6 depicts a schematic diagram of another alternate embodiment of an elastic sensor mesh system for mapping the 3-dimensional shapes of objects in accordance with the present invention.

DETAILED DESCRIPTION OF THE PREFERRED EMBODIMENT

Figure 1:
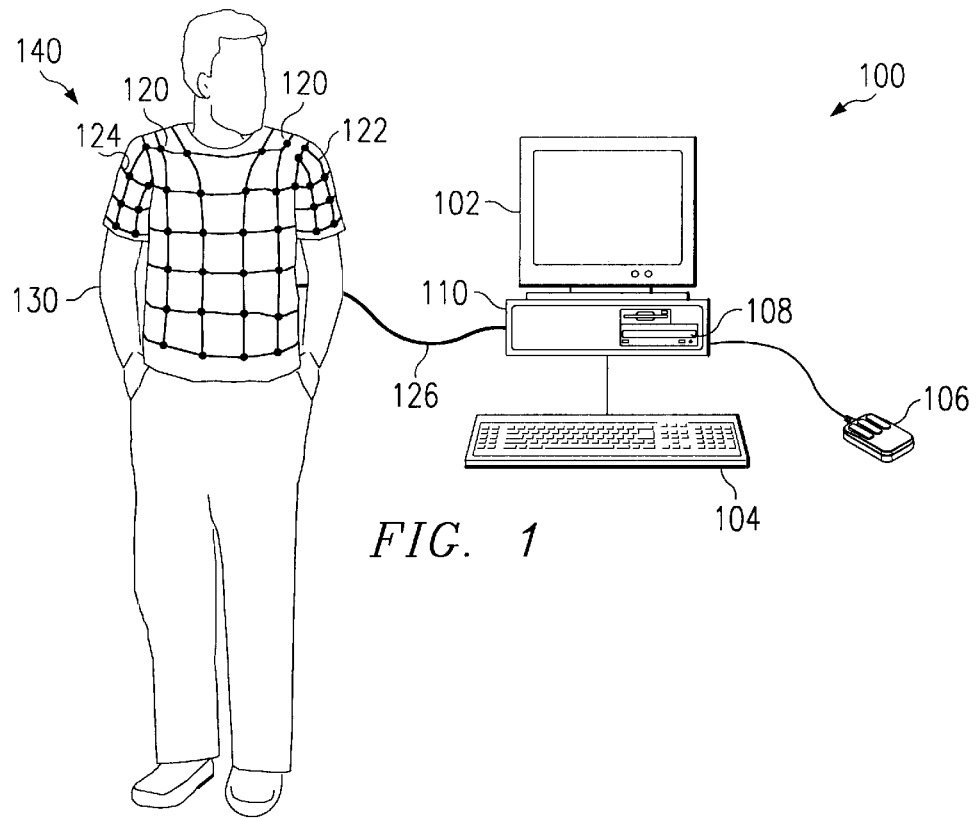
FIG. 1 depicts a pictorial representation of a data processing system and apparatus for determining the 3-dimensional structure of objects in accordance with a preferred embodiment of the present invention.

With reference now to the figures and in particular with reference to FIG. 1, a pictorial representation of a data processing system and apparatus for determining the 3-dimensional structure of objects is depicted in accordance with a preferred embodiment of the present invention. In this example, a personal computer 100 connected by a USB line 126 to an elastic sensor mesh system 140, worn by a person 130 is illustrated. This arrangement allows for the 3-dimensional measurement mapping of the person 130 is depicted.

Elastic sensor mesh 140 includes a plurality of sensors attached to nodes of the mesh sensor 140, such as node 120. Each node is connected to at least one other sensor by elastic connectors, such as, for example, elastic connectors 122 and 124. Elastic sensor mesh 140 initially has a known baseline shape (i.e., the distances and angles between neighboring sensors are known). When elastic sensor mesh 140 is placed over a three-dimensional object, such as, for example the person 130 depicted in FIG. 1, the plurality of elastic connectors expand away from the baseline shape sufficiently to conform to the shape and size of the object for which modeling of the three dimensional shape is desired. The elastic sensor mesh 140 should be somewhat smaller than the object for which the three dimensional shape is desired such that after expansion of the elastic connectors, the elastic sensor mesh 140 fits snugly around the mapped object. Any loose areas in elastic sensor mesh 140 will result in a distorted generation of the picture of the object such that a true representation of the object cannot be obtained.

Each of the plurality of sensors, which may be located at a node, such as, for example node 120, or between a pair of nodes, collects data regarding the distance and the angle to each adjacent sensor. This information is collected and passed through USB line 126 to personal computer 100, where it is then analyzed and a 3-dimensional image of the object, in this case, the torso of person 130, is generated using any number of algorithms. Such algorithms for generating a 3-dimensional image based on the relation of a series of points to other points are well known to those of ordinary skill in the art and many of which may be found in the public domain.

Taking readings of this data, an accurate 3-dimensional mapping of the form can be done by analyzing the sensor data from the deformed mesh and comparing it with the base-line data. The amount of computing power needed to perform this function is quite modest by current standards and, as discussed above, the algorithms are well known.

In one coordinate system, the linear (X-Y) coordinates are directly available as a function of the stretch movement of each segment of elastic sensor mesh 140. The X-Y coordinates correspond to orthogonal directions on the surface of the elastic sensor mesh 140. The Z-coordinate, which is defined as a direction normal from the surface of the elastic sensor mesh 140, may be calculated by calculating the interior angle from the lengths of any two sides of the triangle that is formed at each node. The only information now missing is whether the mesh was pushed in or pushed out. However, since the mesh is always constructed such that it is, in its normal form, smaller than the object on which it is to be worn, the Z-coordinate movement is always in the outward direction. The number of sensors used within elastic sensor mesh 140 may vary according to the application. For example, for determining measurements for tailoring clothing, where fit needs to be accurate, the number of sensors per unit area may be more dense. For athletic form comparison and training, the sensors may be further apart and less dense since the objective in this application is to conform fairly gross motions and form to an ideal motion and form. One of the more densely packed sensor configurations may be for gloves, where the movements are transmitted to a computer system for virtual reality or telepresence applications.

Another application of the present invention is for use in gathering data to build custom shipping containers. The object to be shipped is measured with the elastic sensor mesh 140 at a remote location. The measurements are transmitted to a manufacturer for construction of the necessary close-fitting packing material. The packing material is then placed into an empty container and shipped to the location where the object is located, from which the object can be packed and shipped to its final destination.

With respect to collecting and analyzing data from elastic sensor mesh 140, personal computer 100 includes a system unit 110, a video display terminal 102, a keyboard 104, storage devices 108, which may include floppy drives and other types of permanent and removable storage media, and a pointing device 106, such as a mouse. Personal computer 100 also includes a USB adapter to receive data via USB wire 126. Alternatively, other data transmission devices other than USB wire 126 may be used for transferring data from elastic sensor mesh 140 to personal computer 100, such as, for example, other wire type devices and wireless communication devices. Additional input devices may be included with personal computer 100, as will be readily apparent to those of ordinary skill in the art.

The personal computer 100 can be implemented using any suitable computer. Although the depicted representation shows a personal computer, other embodiments of the present invention may be implemented in other types of data processing systems, such as for example, mainframes, workstations, network computers, laptop computers, and palm computers. Computer 100 also preferably includes a graphical user interface that may be implemented by means of systems software residing in computer readable media in operation within computer 100.

Although elastic sensor mesh 140 has been depicted as having a USB connection to computer 100, other means of transferring the information gathered by elastic sensor mesh 140 to computer 100 may be used as well. For example, USB line 126 may be a fire-wire connection from a central collection device built into the webbing of elastic sensor mesh 140. Alternatively, the data may be transferred to computer 100 using a wireless communication mechanisms, such as, for example, the 900 MHz communication standard utilized by cordless telephones. The method of transmitting the information from the elastic sensor mesh 140 to the computer 100 depends on the application and the amount of mobility required.

It should be noted that while the present invention has been described with reference to mapping the 3-dimensional shape of a human torso, the present invention is not limited to such. The present invention may be utilized to map the 3-dimensional shape of other animate or inanimate objects. The elastic sensor mesh may be tailored to match the general shape for which the 3-dimensional shape is desired to be mapped. For example, the elastic sensor mesh may be tailored to resemble a shirt in order to map the 3-dimensional shape of a human torso or to a generic shape (e.g., a tube with small diameter and great elasticity) for mapping the 3-dimensional shape of non-specific objects.

Figure 2:
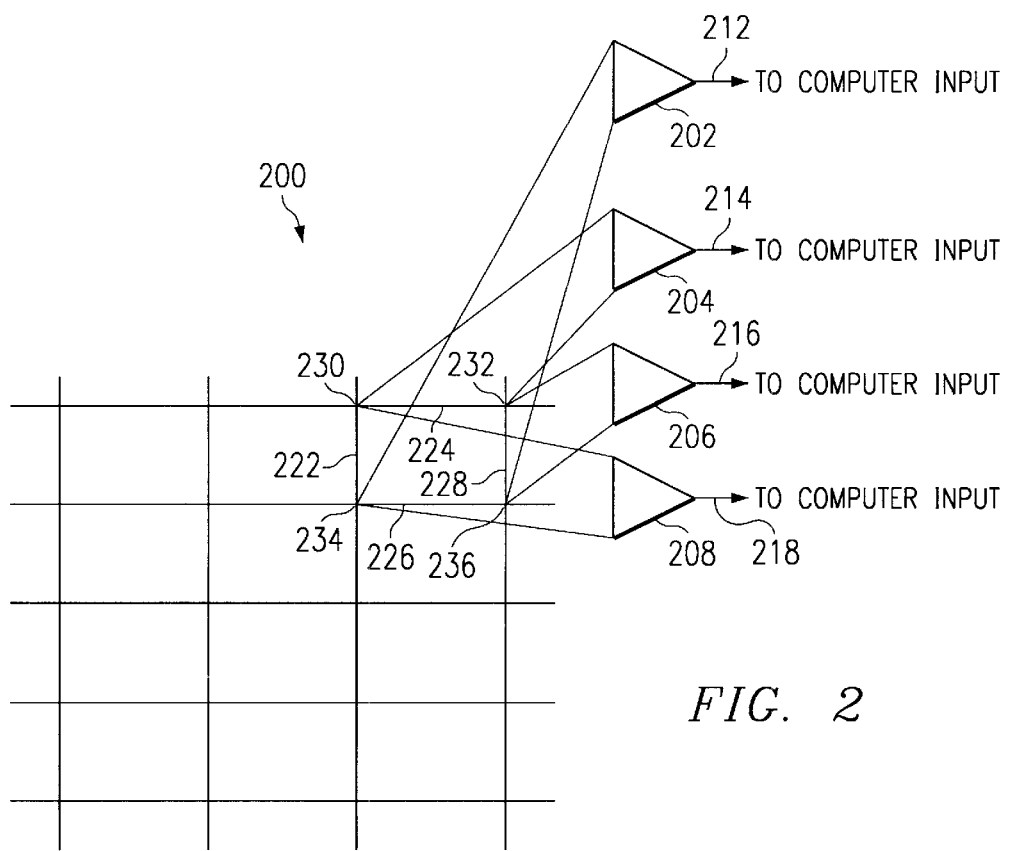
FIG. 2 depicts a block diagram of an apparatus for determining the shape of a 3-dimensional object in accordance with the present invention.

With reference now to FIG. 2, a block diagram of a elastic sensor mesh apparatus for determining the shape of a 3-dimensional object is depicted in accordance with the present invention. Elastic sensor mesh 200 is an example of an elastic sensor mesh, such as, for example, elastic sensor mesh 140 in FIG. 1. Elastic sensor mesh 200 is made up of elastic wire segments, such as, elastic wire segments 222–228. Each of elastic wire segments 222–228 comprises elastic wire of the kind used in strain gauges. A strain gauge wire provides increasing resistance to voltage as it is stretched. Alternatively, the strain gauge may be incorporated within the individual sensors to measure strain in the connections to the other segments.

Each pair of nodes 230–236 at each end of elastic wire segments 222–228 is Ad connected to one of comparator operation amplifiers (op-amps) 202–208. For example, comparator op-amp 202 is connected to node 234 and to node 236 such that the change in voltage across elastic wire segment 226 may be determined. Each of comparators 202–208 sends an output signal along signal lines 212–218 to an analog-to-digital converter (ADC) input of the computer. The output signal is the change in voltage across the two monitored points, such as nodes 234 and 236, as the segment, such as segment 226, stretches from its normal position. Based on similar inputs from each of the segments and the identifications (IDs) of the comparators 202–208 involved, the computer calculates the 3-dimensional movement of the mesh 200 from its known, normal baseline configuration.

Elastic sensor mesh 200 is given as an example of a elastic sensor mesh and is not intended as an architectural limitation of the present invention. Many other types of sensors may be used and perform equally as well as that presented herein. The basic requirement of a sensor is that the sensor is able to sense the distance and angle to the adjacent sensors. The accuracy and density of sensors is dependent upon the type of application for which the mesh sensor is to be used.

Figure 3:
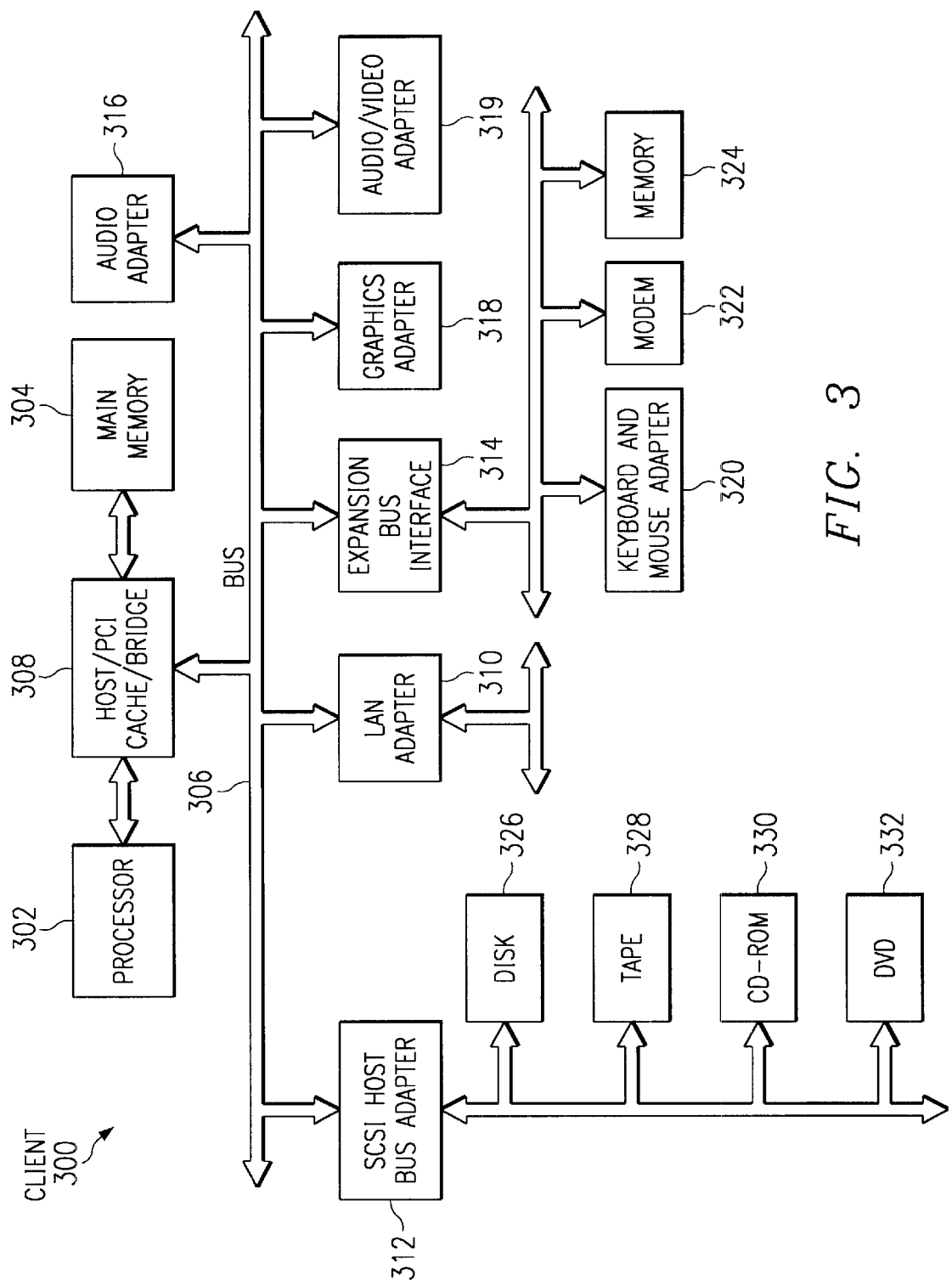
FIG. 3 depicts a block diagram of a data processing system in which some of the processes of the present invention may be implemented.

With reference now to FIG. 3, a block diagram of a data processing system in which some of the processes of the present invention may be implemented is illustrated. Data processing system 300 is an example of a computer, such as computer 100 in FIG. 1, in which data taken from a 3-dimensional measuring device can be processed. Data processing system 300 employs a peripheral component interconnect (PCI) local bus architecture. Although the depicted example employs a PCI bus, other bus architectures, such as Micro Channel and ISA, may be used. Processor 302 and main memory 304 are connected to PCI local bus 306 through PCI bridge 308. PCI bridge 308 may also include an integrated memory controller and cache memory for processor 302. Additional connections to PCI local bus 306 may be made through direct component interconnection or through add-in boards. In the depicted example, local area network (LAN) adapter 310, SCSI host bus adapter 312, and expansion bus interface 314 are connected to PCI local bus 306 by direct component connection. In contrast, audio adapter 316, graphics adapter 318, and audio/video adapter (A/V) 319 are connected to PCI local bus 306 by add-in boards inserted into expansion slots. Expansion bus interface 314 provides a connection for a keyboard and mouse adapter 320, modem 322, and USB interface 324 for receiving the position data of nodes within an elastic sensor mesh, such as, for example, elastic sensor mesh 140 in FIG. 1.

In the depicted example, SCSI host bus adapter 312 provides a connection for hard disk drive 326, tape drive 328, CD-ROM drive 330, and digital video disc read only memory drive (DVD-ROM) 332. Typical PCI local bus implementations will support three or four PCI expansion slots or add-in connectors.

An operating system runs on processor 302 and is used to coordinate and provide control of various components within data processing system 300 in FIG. 3. The operating system may be a commercially available operating system, such as OS/2, which is available from International Business Machines Corporation. "OS/2" is a trademark of International Business Machines Corporation. An object oriented programming system, such as Java, may run in conjunction with the operating system, providing calls to the operating system from Java programs or applications executing on data processing system 300. Instructions for the operating system, the object-oriented operating system, and applications or programs are located on a storage device, such as hard disk drive 326, and may be loaded into main memory 304 for execution by processor 302.

Those of ordinary skill in the art will appreciate that the hardware in FIG. 3 may vary depending on the implementation. For example, other peripheral devices, such as optical disk drives and the like, may be used in addition to or in place of the hardware depicted in FIG. 3. Furthermore, other devices, such as, for example, a wireless communications interface, may be used in place of USB 324 for receiving data from elastic sensor mesh 140. The depicted example is not meant to imply architectural limitations with respect to the present invention. For example, the processes of the present invention may be applied to multiprocessor data processing systems.

Figure 4:
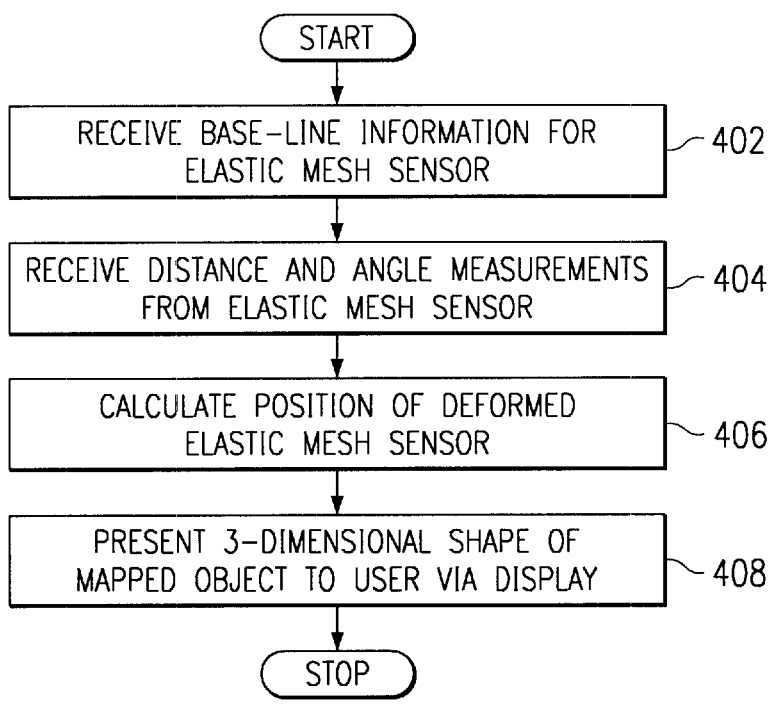
FIG. 4 depicts a flowchart illustrating a method of receiving data from an elastic sensor mesh and constructing and 3-dimensional image from that data in accordance with the present invention.

With reference now to FIG. 4, a flowchart illustrating a method of receiving data from an elastic sensor mesh and constructing and 3-dimensional image from that data is depicted in accordance with the present invention. The process illustrated in FIG. 4 may be performed on a data processing system, such as, for example, data processing system 300 in FIG. 3, which may be used in conjunction with an elastic sensor mesh, such as elastic sensor mesh 200 in FIG. 2.

To begin, the computer receives base-line information for the elastic sensor mesh being utilized (step 402). This base-line information identifies the beginning normal shape of the elastic sensor mesh, which is needed in order to determine the displaced shape of the sensor after deformation around a 3-dimensional object. This base-line information may be transmitted by the elastic sensor to the computer or may be input by a user.

Next, the computer receives distance and angle measurements from the elastic sensor mesh (step 404). The distance and angle measurements indicate the distance and angle by which neighboring nodes of the mesh have been separated as a result of the distortion of the elastic sensor mesh being placed around a 3-dimensional object. The computer then calculates the position of each node in the deformed elastic mesh from which a 3-dimensional representation may be generated (step 406). The generated 3-dimensional image of the mapped object is then presented to a user via a display (step 408). The image presented to the user is actually a 2-dimensional simulation of the 3-dimensional object, but with appropriate shading or other indication to indicate the 3-dimensional character of the object. Furthermore, the image presented to the user may be manipulated to present differing views to the user. Also, other images may be overlaid with the image of the 3-dimensional object mapped, such that the two images may be compared.

Figure 5A:
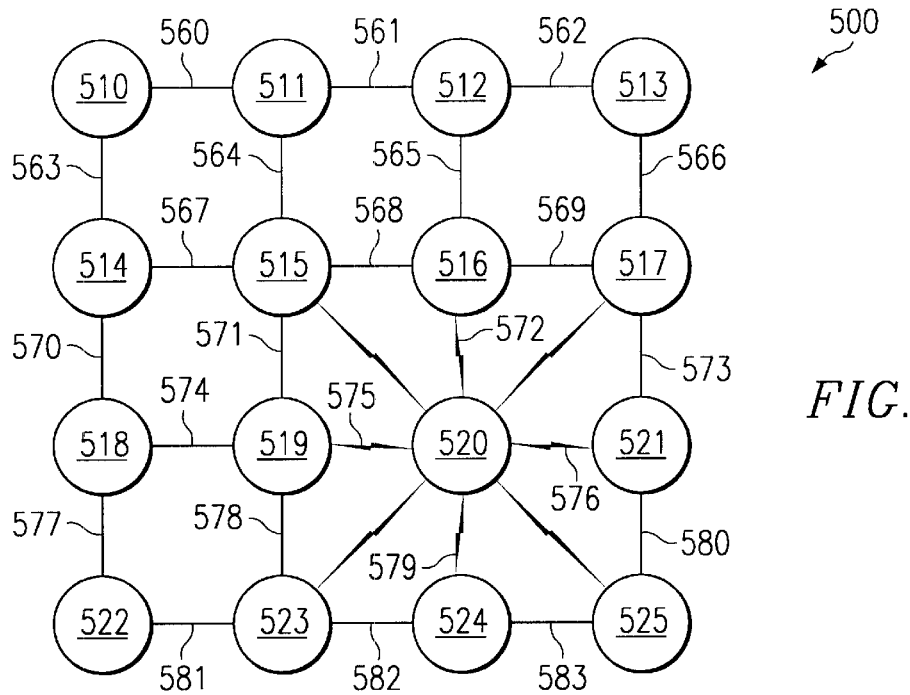
FIGS. 5A–5B depict schematic diagrams of an alternate embodiment of an elastic sensor mesh configuration in accordance with the present invention.
Figure 5B:
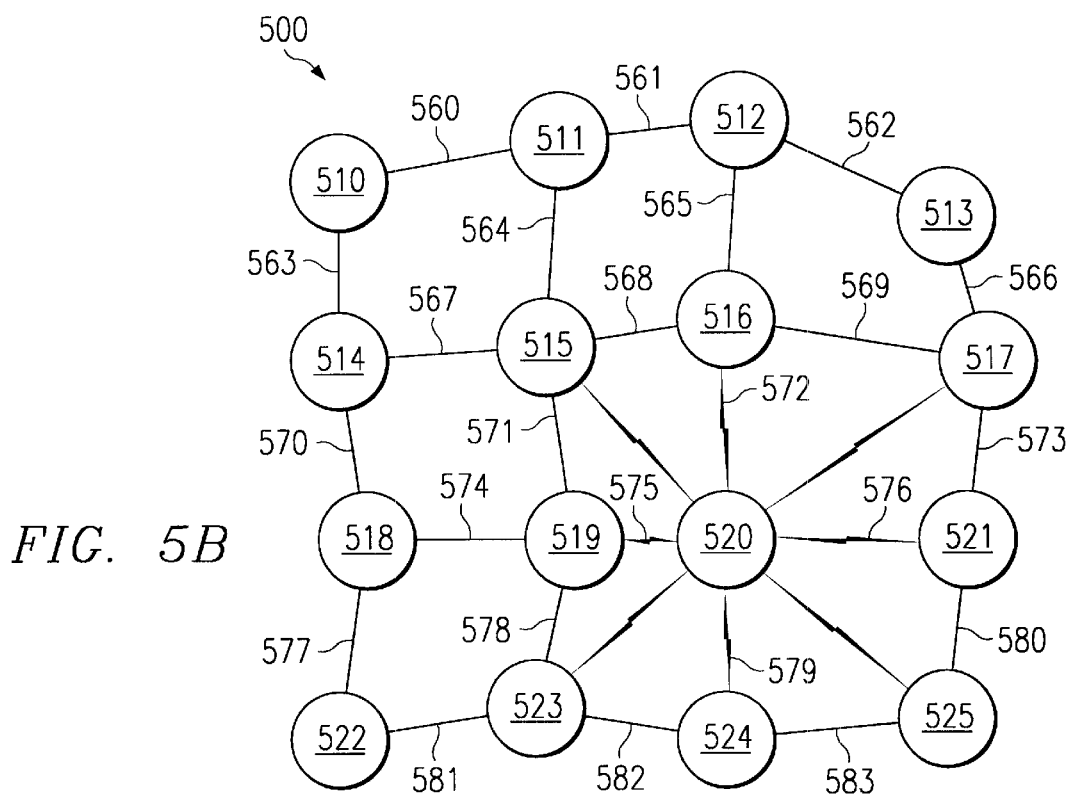

With reference now to FIGS. 5A–5B, schematic diagrams of an alternate embodiment of an elastic sensor mesh configuration are depicted in accordance with the present invention. FIG. 5A depicts elastic sensor mesh 500 in an undeformed state, while FIG. 5B depicts elastic sensor mesh 500 after deformation around a 3-dimensional object. In this embodiment, elastic sensor mesh 500 includes a number of sensors 510–525 each connected to other sensors 510–525 within elastic sensor mesh 500 by elastic connections 560–583. Each of sensors 510–525 emits radio frequency (RF) signals indicating its identity. Each of the sensors 510–525 receives the RF signals from neighboring ones of sensors 510–525 and, using signal strength, sensor identity, and the known initial separation of the sensors 510–525, calculates a relative position. One of the sensors 510–525 may arbitrarily be assigned as the (0,0,0) point as a reference for all other sensors 510–525. The relative position of each of sensors 510–525 is then sent to a computer (not shown) for display and manipulation. The known initial separation may be programmed into each of sensors 510–525 or may be determined by each sensor prior to deformation around a 3-dimensional object using the signal strength and sensor identity for each signal received.

With reference now to FIG. 6, a schematic diagram of another alternate embodiment of an elastic sensor mesh system for mapping the 3-dimensional shapes of objects is depicted in accordance with the present invention. In this embodiment, elastic sensor mesh system 600 includes an elastic sensor mesh 602, three fixed RF sources 640–644, and computer 630. Elastic sensor mesh 602 includes a plurality of sensors 610–625 each connected to others of sensors 610–625 by elastic connections 660–683. Each sensor calculates its relative position to fixed radio frequency sources 640–644 by receiving RF signals from each of radio frequency sources 640–644 and triangulating its position. The position of each of sensors 610–625 is then sent to computer 630 for display and manipulation.

Figure 7:
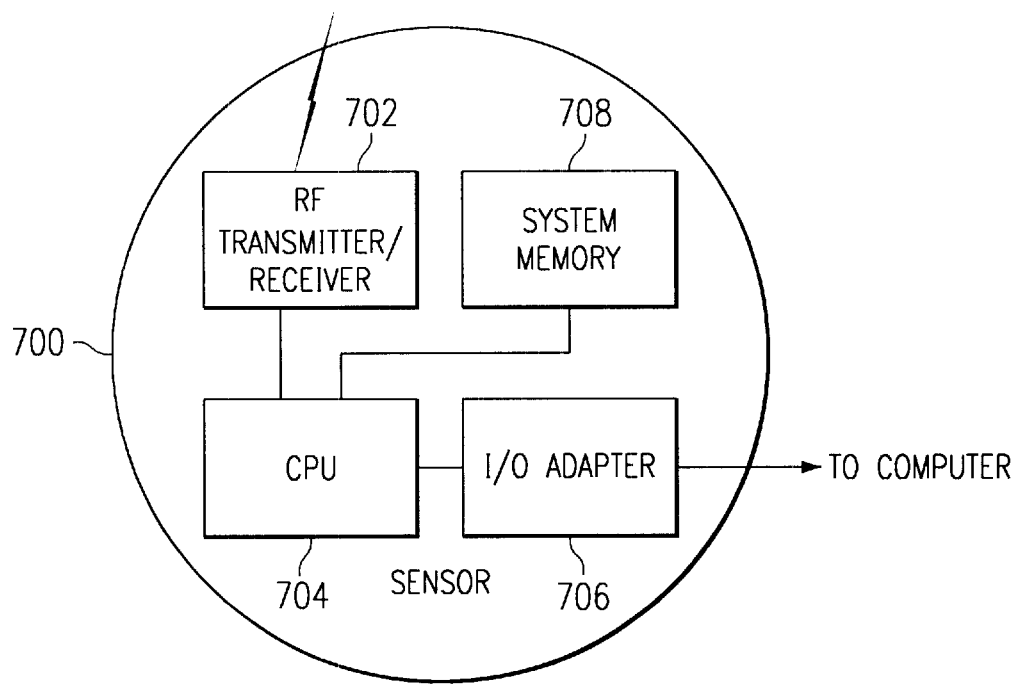
FIG. 7 depicts a block diagram of a sensor for use in an elastic sensor mesh system in accordance with the present invention.

With reference now to FIG. 7, a block diagram of a sensor for use in an elastic sensor mesh system is depicted in accordance with the present invention. Sensor 700 is an example of a sensor that may be used for determining its position relative to other sensors within an elastic sensor mesh, such as, for example, elastic sensor mesh 500 depicted in FIGS. 5A–5B or elastic sensor mesh 602 depicted in FIG. 6. Sensor 700 includes an RF transmitter/receiver 702 for transmitting signals to other sensors and for receiving signals from other sensors or from fixed RF sources, such as, for example, fixed RF sources 640–644 depicted in FIG. 6. Sensor 700 also includes a CPU 704 for executing instructions contained within system memory 708 for calculating the position of sensor 700 based on information received by RF transmitter/receiver 702. The position of sensor 700 is sent to a computer for display to a user and for manipulation, if desired, via I/O adapter 706. I/O adapter 706 may provide for a wired connection via, for example, a USB line, or may provide for wireless infrared (IR) or RF transmission to the computer.

In one embodiment of the present invention, an elastic sensor mesh is utilized to provide input to a computer for interpreting and/or translating American Sign Language (ASL). An elastic sensor mesh, such as described above, perhaps in the shape of a long-sleeved shirt with integrated gloves, is fitted to and worn by an ASL capable person. The elastic sensor mesh is connected to a computer, either by wire or wirelessly. As the person performs ASL, the position information of the arms, hands, and fingers of the ASL capable person is transmitted to the computer. The position information is then translated into movements by the computer. These movements are then translated by the computer, that has been trained to recognize the movements corresponding to ASL, into English, which may then be placed in the form of text or may be utilized by a speech synthesizer within or connected to the computer, such that persons unable to interpret ASL may, nevertheless communicate with the ASL capable person.

Although described with reference to American Sign Language and to English, the above described process may be applied to any type of language involving interpretation of movement rather than speech and may be translated into any language, such as, for example, German, French, or Japanese. Furthermore, the translation of physical movement is not limited to language, but may also be translated into musical tones, wherein different movements correspond to different tones or may be translated into media other than sound, such as light shows, laser show displays, or images on a video display wherein different movements produce differing visual effects.

Although the present invention has been described primarily with reference to determining a single static 3-dimensional shape of an object, the present invention may also be applied to determine the 3-dimensional motion of an object. In such case, the computer would make repeated measurements of the data received from the elastic sensor mesh, with each successive measurement separated from the previous by a small increment of time. Thus, a 3-dimensional image of the object may be created for each increment of time and-merged to form a moving 3-dimensional image of the object.

It is important to note that while the present invention has been described in the context of a fully functioning data processing system, those of ordinary skill in the art will appreciate that the processes of the present invention are capable of being distributed in the form of a computer readable medium of instructions and a variety of forms and that the present invention applies equally regardless of the particular type of signal bearing media actually used to carry out the distribution. Examples of computer readable media include recordable-type media such a floppy disc, a hard disk drive, a RAM, and CD-ROMs and transmission-type media such as digital and analog communications links.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A measurement apparatus for determining the shape of a three dimensional object, comprising:

an array of sensors capable of being placed over at least a portion of the surface of the three dimensional object;

elastic connections between each sensor of said array of sensors and at least another sensor of said array of sensors; and a data processing system that generates a two dimensional representation of the three dimensional object based on information obtained from the array of sensors, wherein said array of sensors is capable of deformation to conform to the surface topology of a three dimensional object, and wherein the shape of the three dimensional object is determined based on a relative position of the sensors in the array of sensors after deformation of the array of sensors to conform to the surface topography of the three dimensional object, wherein each sensor of the array of sensors determines position information using electromagnetic transmissions from other sensors of the array of sensors.

2. The measurement apparatus as recited in claim 1, further comprising means for transmitting data collected by the sensors to a data processing system.

3. The measurement apparatus of claim 2, wherein the means for transmitting data is a universal serial bus interface.

4. The measurement apparatus of claim 2, wherein the means for transmitting data is a wireless communications interface.

5. The measurement apparatus of claim 2, wherein each sensor detects a location of an adjacent sensor by detecting a distance to the adjacent sensor.

6. The measurement apparatus of claim 1, wherein each sensor of said array of sensors determines a respective relative position and said respective relative position of each sensor of said array of sensors is transmitted to the data processing system.

7. The measurement apparatus of claim 6, wherein each sensor of said array of sensors broadcasts and receives a radio frequency signal, wherein each radio frequency signal identifies a respective sensor of said array of sensors and wherein each sensor of said array of sensors determines a relative location based on relative strengths of the radio frequency signals received from neighboring sensors in the array of sensors.

8. A measurement apparatus comprising:

a meshing, including:

a plurality of sensors, wherein each of the plurality of sensors detects a location of an adjacent sensor within the plurality of sensors and is capable of being placed over at least a portion of the surface of a three dimensional object;

a set of deformable connectors, wherein the set of deformable connectors interconnect the plurality of sensors to form the mesh, wherein the mesh is deformable to conform to a surface of the three dimensional object; and an interface connected to the mesh, wherein interface provides a connection to output data generated by the mesh to a data processing system, and wherein the shape or the three dimensional object is determined based on a relative position of the sensors in the array of sensors after the deformation of the array of sensors to conform to the surface of the three dimensional object, wherein each sensor of the plurality of sensors determines position information using electromagnetic transmissions from other sensors of the plurality of sensors and the data processing system generates a two dimensional representation of the three dimensional object based on the position information from the plurality of sensors.

9. The measurement apparatus of claim 8, wherein the interface is a universal serial bus interface.

10. The measurement apparatus of claim 8, wherein the interface is a wireless communications interface.

11. The measurement apparatus of claim 8, wherein each sensor detects a location of an adjacent sensor by detecting a distance to the adjacent sensor.

12. The measurement apparatus of claim 8, wherein each sensor determines a respective relative position and said respective relative position of each sensor is transmitted to the data processing system.

13. The measurement apparatus of claim 12, wherein each sensor broadcasts and receives a radio frequency signal, wherein each radio frequency signal identifies a respective sensor and wherein each sensor determines a relative location based on relative strengths of the radio frequency signals received from neighboring sensors.

14. A system for determining the shape of a three dimensional object, comprising:

a measurement apparatus having a plurality of sensors capable of being placed over the three dimensional object and having means for conforming to the shape of the three dimensional object;

means for determining relative locations of each of the plurality of sensors with respect to others of the plurality of sensors; and means for transmitting the relative locations to a data processing system, wherein each sensor of the plurality of sensors determines position information using electromagnetic transmissions from other sensors of the plurality of sensors, and wherein the data processing system generates a two dimensional representation of the three dimensional object based on the relative locations.

15. A method for determining the shape of a three dimensional object, the method comprising:

receiving position information from a plurality of sensors, said sensors encapsulating at least a portion of the three dimensional object; and generating a two dimensional representation of the three dimensional object, wherein each sensor of the plurality of sensors determines position information using electromagnetic transmissions from other sensors of the plurality of sensors.

16. The method as recited in claim 15, further comprising:
displaying the two dimensional representation of the three dimensional object.

17. The method as recited in claim 15, wherein each of the plurality of sensors is connected to at least one other of the plurality of sensors by an elastic connection.

18. The method as recited in claim 15, wherein the position information comprises a change in distance and angle between each sensor of the plurality of sensors and a plurality of neighboring sensors to each sensor of the plurality of sensors and a predetermined undeformed position of each sensor of the plurality of sensors.

19. The method as recited in claim 15, wherein the position information comprises position information for different points in time and the two dimensional representation comprises a plurality of representation is at least one which corresponds to each point in time.

20. The method as recited in claim 19, wherein the plurality of representations may be presented to a user as an animated graphical display.

21. A method for determining the shape of a three dimensional object, the method comprising:

receiving position information from a plurality of sensors, said sensors encapsulating at least a portion of the three dimensional object; and generating a two dimensional representation of the three dimensional object, wherein the relative position of each sensor of the plurality of sensors relative to a particular sensor of the plurality of sensors is determined by logic within each sensor of the plurality of sensors and the position information comprises the relative position.

22. A computer program product in computer readable media for use in a data processing system for determining the shape of a three dimensional object, the computer program product comprising:

first instructions for receiving position information from a plurality of sensors, said sensors encapsulating at least a portion of the three dimensional object; and second instructions for generating a two dimensional representation of the three dimensional object, wherein each sensor of the plurality of sensors determines position information using electromagnetic transmissions from other sensors of the plurality of sensors.

23. The computer program product as recited in claim 22, further comprising:

third instructions for displaying the two dimensional representation of the three dimensional object.

24. The computer program product as recited in claim 22, wherein each of the plurality of sensors is connected to at least one other of the plurality of sensors by an elastic connection.

25. The computer program product as recited in claim 22, wherein the position information comprises a change in distance and angle between each sensor of the plurality of sensors and a plurality of neighboring sensors to each sensor of the plurality of sensors and a predetermined undeformed position of each sensor of the plurality of sensors.

26. The computer program product as recited in claim 22, wherein the position information comprises position information for different points in time and the two dimensional representation comprises a plurality of representations at least one of which corresponds to each point in time.

27. The computer program product as recited in claim 26, wherein the plurality of representations may be presented to a user as all animated graphical display.

28. A computer program product in computer readable media for use in a data processing system for determining the shape of a three dimensional object, the computer program product comprising:

first instructions for receiving position information from a plurality of sensors, said sensors encapsulating at least a portion of the three dimensional object; and second instructions for generating a two dimensional representation of the three dimensional object, wherein the relative position of each sensor of the plurality of sensors relative to a particular sensor of the plurality of sensors is determined by logic within each sensor of the plurality of sensors and the position information comprises the relative position.

* * * * *